United States Patent [19]

Hidvégi

[11] Patent Number: 5,277,910

[45] Date of Patent: Jan. 11, 1994

[54] PROCESS FOR THE PREPARATION OF A PHARMACEUTICAL COMPOSITION SELECTIVELY LOWERING THE BLOOD-LIPID LEVEL

[76] Inventor: Máté Hidvégi, 63, Hegedüs Gy. u., Budapest 1133, Hungary

[21] Appl. No.: 989,140

[22] Filed: Dec. 11, 1992

[30] Foreign Application Priority Data

Dec. 12, 1991 [HU] Hungary ............................. 3928/91

[51] Int. Cl.$^5$ ............................................. A61K 35/78
[52] U.S. Cl. .................................................. 424/195.1
[58] Field of Search ...................................... 424/195.1

Primary Examiner—John W. Rollins
Attorney, Agent, or Firm—Keil & Weinkauf

[57] ABSTRACT

The invention relates to a process for the preparation of a selective blood-lipid-level-lowering pharmaceutical composition by extraction of the seed, root, stalk and/or leaves of alfalfa. According to the process of the invention, the extraction is carried out with water or an aqueous solution of a temperature of at least 40° C. and a pH of at most 8, whereafter the extract obtained is transformed alone or together with hardly or not digestible polysaccharides and optionally with carriers commonly used in the pharmaceutical industry to a pharmaceutical composition. The composition according to the invention contains neither canavanine (being a toxic amino acid) nor coumestrol (possessing hormone effect).

13 Claims, No Drawings

PROCESS FOR THE PREPARATION OF A PHARMACEUTICAL COMPOSITION SELECTIVELY LOWERING THE BLOOD-LIPID LEVEL

The invention relates to a process for the preparation of a selective blood-lipid-level-lowering pharmaceutical composition by extraction of the seed, root, stalk and/or leaf of alfalfa, optionally by concentrating the extract and optionally preparing a dried powder or granulate from the concentrated extract.

It is known that the most important risk factor of cardiovascular diseases and myocardial infarction, playing a leading role in the mortality statistics of the mankind, is in close relation to the amount of certain blood lipid components adversely influencing the health. This was emphasized also by rewarding Brown and Goldstein with the Nobel prize in 1985 for their new recognition relating to diseases caused by cholesterol. Meanwhile it has become clear from the most important pathological statements published in the literature [Journal of American Medical Association 248, 1465 (1982); ibidem 256, 2835 (1986)] that at the upper limit of the serum cholesterol level, i.e. 6.5 millimol/liter—which had earlier been accepted—, the ratio of patients suffering from ischaemia, i.e. the life-threatening insufficiency of blood supply, is twofold in comparison to those with a concentration of about 5 millimol/liter.

The investigations involving fine details clearing up the role of individual blood lipid components were particularly important. Thus, it has become clear that, in addition to the high level of serum cholesterol (i.e. the so-called hypercholesterolaemia), that of triglyceride-type lipids (hypertriglyceridaemia) as well as the incorrect distribution of the ratio of high-density lipoproteins (HDL) to the low-density lipiproteins (LDL), i.e. the so-called dyslipoproteinaemia, play a decisive role in the coronary diseases of the heart. This was supported inter alia by the investigations of Frick et al. [New Engl. J. Med. 317, 1237 (1987)] showing that not only a twofold but also a threefold decrease in the ischaemic diseases and mortality could be achieved by drug treatments preferably influencing the concentration of the three lipid types mentioned above.

It has been stated by statistical estimations in several countries that the blood lipid levels of about 65 to 76% of the adult population approximated the high-risk level. The average blood chlolesterol level of Hungarian people is 5.6–5.7 millimol/liter [Magyar Tudomány ("Hungarian Science") 3, 265 (1989)]. In the United States, the LDL cholesterol level of 3.4–4.1 millimol/liter is considered to be acceptable for health whereas a higher level is believed to be endangering [Arch. Intern. Med. 148, 36 (1988)].

Hyper- and dyslipoproteinaemia mainly develop as consequences of disturbances in the fat metabolism and can be regulated by drugs. When administered orally, these drugs are absorbed, inhibit the biosynthesis of lipoproteins and increase their decomposition and elimination (such as e.g. the clofibrate or nicotinic acid derivatives); or they are not absorbed from the intestinal tract and inhibit the absorption of lipids therefrom (such as e.g. ion-exchange resins, sitosterol, dextran sulfate and the like). However, these drugs should cure-likely be used and as a consequence nausea, diarrhoea, in other cases constipation, meteorism, muscular pains, potency disturbances, lithogenesis, rarely hair loss and side effects accompanied by skin symptoms may develop.

In the case of hyperlipoproteinaemia meaning a high risk, the drug treatment accompanied by side effects means a lower risk. In opposition to this, a composition being free of side effects, i.e. risk-free, with the desired effectivity would be demanded for subjects who are endangered only in view of the blood lipid level. Such a composition has not been available up to the present. In the course of my systematic investigations the development of a composition class of such type was aimed.

The highest attention was paid to the saponins possessing a promising antilipaemic effect among drugs of plant origin.

Saponins, the plant-physiological role of which is hardly known at present, are found in a high number of plant individuals of the plantage. With a few exceptions, these saponins are toxic to the man.

Similarly, it is known from the literature that the so-called neutral or acidic saponins of vegetable origin are capable of selectively forming complexes with cholic acids or cholesterol and its derivatives [Biochemistry and Function of Isopentenoids in Plants. Monograph (Marcel Dekker, New York, 1984), pages 229–246] and these saponins can be found in a high number of plants.

The chemically best known sapogenin components [CRC Crit. Rev. Food Sci. Nutr. 26, 27–135 (1987)] are soy sapogenol A, B, C, D, E and F to which various sugar moieties are connected in the so-called neutral saponins being present in certain plants. All these are present in the soy and alfalfa whereas a part thereof is found in bean, pea and clover sorts as well as in peanut, Lotus corniculatus and the like. Other neutral sapogenins are avenacin A and B, nuatigenin, isonuatigenin and the like in the oat; solagenin, neochlorogenin, gitogenins, capsicosides, melongosides, jurubin in the potato and capsicum sorts, tomatin in the tomato; sitosterol, amyrin, gitogenins and the like in the onion sorts, chiefly in garlic; officinalysnin and asparasaponins in the asparagus sorts; tea-saponins in the tea plant; diosgenin inter alia in the jam root; aescin, aescinialin, cryptoaescin in the horsechestnut. Other neutral sapogenins are to be found in the fenugreek, yucca, pumpkin, cucumber, blackberry, mulberry, huckleberry, strawberry, horsetail and rose sorts, particularly in hip, common confrey, ginseng root and the like.

The main representatives of acidic sapogenins are oleanolic acid, oleandiolic acid, medicagenic acid, glycirrhizetic acid, epicatonic acid, echinocistoic acid, hederagenin, gypsogenin, medicoside, helianthoside derivatives and the like, containing various sugar moieties in the individual saponins. These can be found in clever sorts, alfalfa, sunflower, onion, garlic, nutmeg, spinach, sugar-beet, sweet-root, Panama plant rind, saponaria, velum, valley lily, clematis and the like.

From the viewpoint of antilipaemic activity, alfalfa can be considered to be the most useful though not single saponin source, since it became known that all of its saponins form a complex with cholesterol [J. Amer. Chem. Soc. 76, 2271 (1954)]; the study of this complex was also published in detail [Biochim. Biophys. Acta 270, 1818 (1972)].

In the broad sense alfalfa (medic) means the Medicago L. genus whereas in the narrow sense it represents the best known, commonly cultivated species of the genus, the fodder alfalfa (blue alfalfa; Medicago sativa L.). Other important home-cultivated species close-related to the latter one are the alfalfa grown on sandy soil (or gaudy alfalfa), the sickle or yellow alfalfa and the black alfalfa.

The axis of the shoot system of the blue and gaudy alfalfa consists of a caulis developing from the rhizome, which ramifies at its basis. The foliage-leaf of the alfalfa species is a digitately composite triple leaf. The leaf standing in various positions is kept by a petiole (leaf-stalk). On the lower leaves of the blue alfalfa the shoulder of the leaflets is wedge-shaped, the leaves show a reverse egg-form.

The inflorescence of the blue alfalfa is a compact cluster usually bearing 8-25 flowers. The axis of inflorescence is frequently longer than the total length of the petiole and leaf-blade. The flower has a characteristic papilionaceous structure. The green calyx consists of five leaves, its surface is usually weakly hirsute. The length of the flowers is about 10 mm. The colour of the corolla of blue alfalfa may show many nuances from light blue up to dark violet-blue.

The seed of blue alfalfa is 2-2.8 mm in length, 1.5-1.7 mm in width and 1.1-1.2 mm in thickness; it has the form of a bean or kidney or an obtuse triangle with a laterally compressed distorted symmetry.

The main components occurring in alfalfa are as follows:

a) Universal proteinogenic amino acids, such as glutamine, asparagine, alanine, arginine, cysteine, glycine, histidine, leucine, lysine, methionine, proline, serine, tyrosine, threonine, tryptophan, phenylalanine and valine.

b) Specific amino acids (most of them are free amino acids though they can be found in a form built into certain proteins): ornithine, citrulline, gamma-aminobutyric, acid, gamma-methyleneglutamic acid, deltahydroxylysine, epsilon-amino-alpha-hydroxycaproic acid and canavanine.

c) Amines: choline and trimethylamine.

d) Fatty acids: linoleic acid, oleic acid, linolenic acid and stearic acid.

e) Phospholipids: lecithin, cephalin and phosphatidic acid.

f) Isoprenoid lipids: sterols and triterpenic saponins.

g) Carotinoids: carotins and xantophylls.

h) Monoterpenes: ocimene (the main fragrance component of alfalfa).

i) Diterpenes: phytol and phylloquinone.

j) Anthocyans: diglycosides of delphinidin, petunidin and malvidin.

k) Among the furocoumarins, significant amounts of coumestrol possessing a high uterotrophic activity are found in the alfalfa. Owing to this fact, the feeding of sheeps with alfalfa can modify the luteinizing hormone level of the animals and can induce sterility and it can even be a risk factor in alfalfa preparations used for human comsumption, too [I. Bócsa and L. Szabó: "Alfalfa and its Relatives" (in Hungarian), Akadémiai Kiadó, Budapest 1987, pp. 79 and 80)].

l) Alfalfa is very rich in alfalfa (medic) saponins, i.e. glycosides formed from pentacyclic sapogenins with various sugars. The most important sapogenins are soy sapogenol A, B, C, D and E as well as alfalfa acid and medicagenic acid. Within the plant the leaves are about twice as rich in saponins as the stalks; whereas the roots contain about ten times more sapogenins than the shoot. The compositions of saponins of the root are different from those of the shoot.

According to the prior art, the saponins are extracted from parts of the alfalfa plant by using aqueous alcohol [The American Journal of Nutrition 30, 2061 (1977); Second Münster International Arteriosclerosis Symposium: Clinical Implications of Recent Research Results in Arteriosclerosis, Westdeutscher Verlag, Münster 1983, p. 242] or alcohol [Phytochemistry 13, 2253 (1974)].

The blood cholesterol level-lowering and lipid-lowering effects of the total saponins extracted from alfalfa stalk and leaf were shown on monkeys [J. Clin. Invest. 67, 156 (1981); Clinical Implications of Recent Research Results in Arteriosclerosis, Westdeutscher Verlag, Münster 1983, pp. 241-254]. The blood cholesterol level- and apolipoprotein level-lowering action in man of the seed-grist of alfalfa was investigated in the Carolinska Institute (Sweden) and it has been stated that a very high concentration value (958-800 millimol/liter) could be decreased by about 17-18% by feeding daily 40 g of the grist [Atherosclerosis 65, 173 (1987)]. However, this effect cannot be considered to be therapeutically sufficient.

Although the extract obtained from parts (seeds, root, stalk and leaves) of the alfalfa plant in the known way, i.e. by extraction with alcohol or aqueous alcohol, can be utilized for lowering the blood cholesterol and lipid levels, it is known that these plant parts contain toxic canavanine [2-amino-4-(guanidinooxy)-butyric acid] [The Merck Index, 11th Edition, (1989) Rahway, N.J., U.S.A., p. 263] and harmful phytoestrogens, chiefly coumestrol (The Merck Index, page 401). Thus, the use of such extracts for therapeutical purposes is accompanied by adverse side-effects.

Canavanine is present in an amount of 1.5% of the dry weight in the seed and young shoots of the alfalfa plant. It induces a syndrome resembling lupus erithemathosus in monkeys fed with alfalfa [Science 216, 415 (1982)].

The commercially available alfalfa tablets prepared from dried alfalfa contain 20-190 ppm of coumestrol. This means that daily more than 1 mg of coumestrol get to the body of consumers of alfalfa tablets who are on this diet: such an amount of this estrogenic hormone can lead to pathological side effects [J. Agric. Food Chem. 32, 173 (1984)].

None of the alfalfa extraction processes known up to the present could eliminate the adverse coumestrol and canavanine contents of the extract.

The present invention is aimed at developing a process which renders possible to prepare from parts of the alfalfa plant an extract containing neither phytoestrogens nor canavanine.

The invention is based on the recognition that the above aim can completely be achieved by extracting the parts of the alfalfa plant with water or an aqueous solution of a temperature of at least 40° C. and of a pH of at most 8.

Thus, the present invention is a process for the preparation of a pharmaceutical composition selectively lowering the blood lipid level by extracting the seed, root, stalk and/or leaves of the alfalfa plant, optionally concentrating the extract and optionally preparing a dried powder or granulate from the concentrated extract. According to the invention the extraction is carried out by using water or an aqueous solution of at least 40° C. and a pH of at most 8 and transforming the extract thus obtained alone or together with hardly or not digestible polysaccharides, colloid-stabilizers, and optionally with carriers commonly used in the pharmaceutical industry, to a pharmaceutical composition.

According to a preferred embodiment of the process of the invention the extraction is carried out by using an aqueous solution of a temperature of 50°-120° C. and a pH of 5.5-6.5, more preferably a temperature of 60°-70° C. and a pH of 5.8-6.2.

It is suitable to use an acidic buffer solution as aqueous solution, preferably an aqueous solution containing acetic acid and sodium acetate; or potassium dihydrogen phosphate and disodium hydrogen phosphate; or disodium hydrogen phosphate and citric acid.

For the extraction it is preferable to use an aqueous solution of hydrochloric, acetic, citric, malic, tartaric, succinic or ascorbic acid or a salt of these acids or sulfuric acid formed with iron, magnesium, calcium, manganese, selenium, zinc, cobalt and/or copper ions, or a salt of the above ions formed with aspartic or glutamic acid.

It is preferable to prepare an extract from the leaves of alfalfa or from dried leaf powder by extracting with a tenfold amount of water of a temperature of 95°-100° C. for 25-35 minutes. After filtering the extract the whole amount of the surface-active agents is extracted by a half volume of butanol in several portions. The butanolic phases are combined and evaporated to dryness To the dry extract an acidic flavouring agent, preferably citric acid, a sweetening agent, suitably aspartame, an aromatizing agent, preferably spearmint and thyme extract, as well as a colloidal emulsion-stabilizer, preferably maltodextrin, are added in a ratio resulting in an amount of 1.5-30% by weight, preferably 14% by weight of the gravimetrically weighed total saponins in relation to the dry material in the final product.

The thus-obtained product containing 14% by weight of saponin was subjected to various examinations. First, it was detected by a method known from literature [Analyst 114, 965 (1989)] that canavanine, the toxic amino acid occurring in alfalfa, could not be found in the product. Similarly, it was investigated whether the product contained coumestrol, i.e. the other toxic substance characteristic of alfalfa [J. Agric. Food Chem 32, 173 (1984)]. No coumestrol could be detected in the product, either.

Since the product is innocuous to such a degree that the so-called acute toxicity, i.e. the dose causing a mortality of 50% ($LD_{50}$ value), could not be determined, a so-called subchronic 70-day toxicity study was carried out with the product on male Sprague-Dawley rats weighing about 160 g each. Two groups consisting of 12 animals each were formed, one of which served as control, whereas 15% by weight of the above product calculated for the dry material were mixed to the food of the other group.

The average daily food consumption agreed in both groups and amounted to a daily average of 28.0 g (with the limit daily values of 21.4 and 37.3 g, respectively). Thus, the dose level of the subchronic toxicity investigation corresponded to 3.67 g (with the limit values of 2.81 g and 4.81 g, respectively) total saponins/kg of body-weight/day.

During the 70-day study no perishment was observed in either of both groups. No significant difference between the two groups was found in the blood sugar, urea, uric acid, creatinine, sodium, potassium, chloride, carbon dioxide, calcium, phosphor, total protein, albumin, bilirubin, alkaline phosphatase, erythrocyte, haematocrit and haemoglobin values being characteristic of the haematological state. However, a blood cholesterol level lower by 18.7% and triglyceride level lower by 5.6% in comparison to the control developed in the group fed with saponin.

In organ examinations no visible pathological changes were detected in the liver, stomach, kidney, spleen, lungs, heart and brain; no significant differences in the organ weights were observed between the two groups. Therefore, histological examinations were not performed.

The neutral and acid saponins of the whole of active ingredients of the product were examined by thin-layer chromatography (TLC) as follows:

1.0 g of product was dissolved on heating in 100 ml of distilled water and extracted 5 times with 10 ml of n-butanol each. The combined butanol phases were evaporated under reduced pressure to dryness with an analytical accuracy. The residue represented the gravimetrically weighed total saponin active ingredient content. This residue was dissolved in 50 ml of methanol and used for chromatographic examination under the conditions described hereinafter.

Layer: silica gel G (Merck)
Developing system: butanol+ethanol++concentrated ammonia (35+15+30)
Time of saturation: 60 minutes in a bath covered with filter paper
Developing time: 4 hours
Running distance: 160 mm
Application: 25 µl of methanolic solution Since acidic or neutral saponins are capable of selectively form an emulsion complex with cholesterol or cholic acids and so they inhibit the absorption of lipids from the gastrointestinal system, an in vitro measurement method was developed for determining the emulsifying capacity of the whole amount of saponins.

According to chromatographic investigations, the total amount of saponins of 14 ($\pm 0.2$) % by weight gravimetrically determined in the above product prepared by the process of the invention was composed of 8 saponins being present in various ratios. 200 mg of this product were dissolved in 10.0 ml of water and mixed with various amounts (mg) of sunflower oil (Sunflower Seed Oil Sigma S 5007, Sigma, St. Louis, Mo., USA). The sample was vigorously shaken at 35° C. on a laboratory machine for minute, then the relative turbidity of the emulsion formed was determined as percentage ([%]) in comparison to the sample containing oil ["Physico-Chemical Practicum" (in Hungarian), Tankö nyvkiadó, Budapest 1968, Vol. 11, p. 316]. The measuring data ar summarized in the following Table:

| [mg] | 0 | 10 | 20 | 40 | 60 | 80 | 100 |
|---|---|---|---|---|---|---|---|
| [z %] | 60 | 8.5 | 4.5 | 2.5 | 1.7 | 1.3 | 1.1 |

The data pairs can be expressed by the following general equation showing a saturation function in its character:

$$[z\%] = a.(mg)^{-1/n}$$

where a and n are parameters depending on the measuring method and the emulsifying capacity of the substance tested, the values of which amounted in our measurements to a=60 and n=1.19, resp.

On the basis of examinations on a high number of samples it has been stated that the parameter n was influenced by the weight ratios and the physical manner of shaking (e.g. mechanical or magnetostriction- or ultrasound-generated shaking and the like) used in the test, but the emulsifying capacity of the sample tested could correctly be judged by using comparative tests (carried out in the same manner). Thus, the experimental data could always be expressed by the above general equation and the value of n was inversely proportional to the emulsifying capacity. A very weakly surface-active sample possessed low emulsifying capacity and in this case n reached even a value of 10-15. By using a sample with a high surface activity the value of n was close to 1, eventually lower than 1.

By using this method it could be elucidated that hardly or not digestible polysaccharides were capable to increase the emulsifying capacity of the whole of saponins because they stabilized the emulsified colloidal grains and therefore they synergistically increased the emulsifying capacity of saponins and hydrophilic-lipophilic-type components (such as flavonoids, carotinoids, terpenoids and the like). Consequently, the antilipaemic biological effectivity of all the active agents was increased.

Based on these observations, according to an other preferred embodiment of the process of the invention the product contains also hardly or not digestible polysaccharides dissolving in polar solvents and moderately dissolving in nonpolar solvents, in addition to the acidic and neutral saponins. This product is conveniently prepared in such a way that the leaved shoot of the purified alfalfa is ground in dry state and then it is infused with a tenfold volume of boiling water for 1 hour and filtered after cooling. Then, 55 parts by weight of maltodextrin, 5 parts by weight of barley-beta-glucan, 5 parts by weight of oat-beta-glucan, 4 parts by weight of apple pectin, 4 parts by weight of citric acid, 1.5 parts by weight of ascorbic acid and 0.5 part by weight of an artificial sweetening agent, calculated for 25 parts by weight of the total saponin content, are added to the filtrate. This liquid-phase intermediate is spray-dried or dried by microwave under reduced pressure or by simple evaporation to dryness and processed to a solid-phase product.

The capacity of inhibiting the lipid absorption of the product prepared in this way was investigated by using the in vitro method described above. The value of the parameter n characterizing the emulsifying capacity according to the test meethod was found to be 1.05, a value representing a very good qualification.

Investigations lasting for 1 month were carried out with this product. Nineteen voluntary persons of an age between 31 and 63 years (14 men and 5 women) consumed daily $2 \times 1$ g of this product distributed in 100 ml of water after eating in the morning and in the evening. The following results of blood lipid parameters (as millimol/liter) were obtained before and at the end of the study:

|  | Starting values | | After 1 month | | Difference ±% |
| --- | --- | --- | --- | --- | --- |
|  | Mean | Limits | Mean | Limits |  |
| Blood cholesterol | 6.80 | 4.70–11.20 | 4.70 | 3.92–7.15 | −30.9 |
| Triglycerides | 1.72 | 0.54–5.60 | 1.58 | 0.57–4.20 | −8.2 |
| HDL | 1.53 | 1.07–2.20 | 1.63 | 1.00–2.43 | +7.9 |
| LDL | 4.10 | 3.13–7.95 | 2.90 | 2.08–5.36 | −29.3 |

It has been stated that the composition prepared according to the process of the invention stimulates the liver to an enhanced decomposition of blood cholesterol. In my supposition this can be attributed to a selective specific stimulatory effect not published in the literature up to now. As a result of this effect hyperlipaemia and mainly the endangering dyslipoproteinaemia can be influenced with a favourable selectivity since the total cholesterol level and within this the LDL level are lowered but the HDL level is elevated. A further advantage of the composition is that it lowers the triglyceride level.

The extract prepared according to the process of the invention can be used alone or together with other known active agents being useful for lowering the blood-lipid level. As unambiguously shown by my above experiments, a particularly preferable effect can be achieved by using the extract prepared by the process of the invention together with polyoxide- and/or carbohydrate-type colloid-stabilizing agents.

For the therapeutical use the extract prepared by the process of the invention is transformed alone or in combination with other similarly acting agents to pharmaceutical compositions being useful mainly for oral administration by mixing it with non-toxic solid or liquid carriers and/or other additives commonly used in the pharmaceutical industry and transforming the mixture obtained to a liquid composition, suitably solution, syrup, suspension or gel. The solid-phase water-miscible granulates, tablets, hard-gelatine or soft-gelatine capsules, suppositories and the like can similarly be prepared.

The preparation of pharmaceutical compositions is carried out by known methods of the pharmaceutical industry, by mixing the extracts with inert inorganic or organic, solid or liquid carriers and then transforming the mixture to a galenic form.

Lactose, maize starch, potato starch, talc, magnesium carbonate, magnesium stearate, calcium carbonate, stearic acid and salts of stearic acid are useful carriers for the preparation of tablets, dragées and hard-gelatine capsules. It is suitable to use vegetable oils, fats, waxes or appropriate polyols as carriers in soft-gelatine capsules. Water, polyols, sucrose or glucose are suitable carriers for the preparation of solutions and syrups. Oils, waxes, fats or polyols with an appropriate consistency can be employed as carriers for preparing suppositories.

The pharmaceutical compositions may contain other additives commonly used in the manufacture of pharmaceuticals, e.g. wetting, sweetening and aromatizing agents, buffers and the like.

The daily dose of the pharmaceutical compositions containing the extract prepared by the process of the invention can be varied between broad limits depending on several factors such as the activity of the active agent, state and age of the patient and the like. For adult patients, the oral dose consists of a composition containing 30–1200 mg, preferably 300–400 mg, of saponin. However, these doses are only of informative character and the dose to be administered should be determined by the physician in every case.

In the therapeutical use, the extracts prepared by the process of the invention are mainly administered orally in the form of tablets or capsules or water-soluble granulates or tablets.

The main advantages of the process according to the invention are as follows:

a) It renders possible the preparation of an alfalfa extract containing at most 9 ppm of coumestrol and at most 1 ppm of canavanine.

b) The extracts prepared by the process of the invention contain the neutral and acidic saponins being present in the parts of the alfalfa plant in a favourable ratio. Thus, in comparison to alfalfa extracts known till now, significantly better therapeutic results can be attained by using the extracts in the treatment of hyper- and dyslipoproteinaemia.

c) The specific blood-lipid-level-influencing effect can be synergistically strengthened by combining the thus-prepared extract with hardly or not digestible polysaccharides.

The process according to the invention is illustrated in detail by the aid of the following non-limiting Examples.

EXAMPLE 1

5×100 kg of dried alfalfa leaves or shoot ground to grade III sieve-mesh were processed. The extraction was carried out in an acid-resistant cylindrical extractor of a volume of 4 m$^3$. After introducing 1 m$^3$ of preheated water of 90° C. into the apparatus, the temperature of water was increased to 100° C. by directly introducing steam, then the first portion of 100 kg of the plant parts was fed in and the extraction was carried out at 100° C. under stirring for 10 minutes.

The filtrate was separated from the plant residue by using an Alfa-Laval screw decanter. The dry material content of the solution obtained was found to be 2.5–3% by weight by refractometric determination. The other four portions of 100 kg each were extracted and decanted in the sam way, then the solutions obtained were combined.

The combined solutions of pH 5.9 were concentrated to a dry material content of 22–28% by weight at 40°–45° C. in a continuously operated evaporator under reduced pressure. The dry material content was refractometrically observed. The total dry material content was calculated after determining the volume and the specific weight.

To this concentrate 13.5% by weight of maltodextrin (calculated on the plant dry-material content) dissolved in water were added as spray-drying additive, then it was spray-dried with an inlet temperature of 170°–180° C. and an outlet temperature of 90° C.

To the powder obtained, 17.5% by weight of ground citric acid monohydrate and 1.2% by weight of aspartame were portionwise added and these components were uniformly mixed with the base powder in a Lödige-type homogenizer.

After granulating, the powder thus obtained can be directly formulated as an instantaneous tea composition.

EXAMPLE 2

The process described in Example 1 was followed with the difference that the extraction was carried out by boiling an aqueous solution of pH 4.6 containing 0.1 mol/liter of acetic acid and 0.1 mol/liter of sodium acetate.

EXAMPLE 3

The process described in Example 1 was followed with the difference that the extraction was performed by using an aqueous solution of pH 2.0 containing 0.01 mol/liter of hydrochloric acid.

EXAMPLE 4

The process described in Example 1 was followed with the difference that the extraction was carried out for 15 minutes by using water preheated to 40° C., the combined solutions obtained after decanting were heated to boiling and filtered through a filter press. After concentrating as described in Example 1, the filtrate was spray-dried. After granulation the powder obtained was compressed to tablets weighing 800 mg each.

EXAMPLE 5

The process described in Example 4 was followed with the difference that the extraction was carried out by using an aqueous solution of pH 5.8 containing 2 g/liter of selenium aspartate and after concentrating no spray-drying was performed but 0.5% by weight of potassium sorbate and 0.5% by weight of aspartame were added to the concentrate.

The solution obtained can be used as a syrup.

EXAMPLE 6

A 50 kg portion from 800 kg of purified and ground leaved alfalfa grist was stirred with 3 m$^3$ of water of 40° C. for 1 hour and then filtered. The plant sludge was pressed out, and after combining with the filtrate the press liquor was supplemented, if necessary, to 3 m$^3$ with water and a next portion of 50 kg of alfalfa grist was suspended therein. After repeatedly stirring, filtering and pressing, the procedure was repeated until the processing of the total amount of 800 kg of alfalfa grist. The filtrate of pH 6.0 obtained in the last step was heated to boiling and filtered. After adding 68 kg of emulsion-stabilizing polysaccharide, 25 kg of citric acid monohydrate and 4 kg of aspartame, the filtrate was heat-treated at 120° C. in an autoclave for 40 minutes. After cooling to 15° C. the mixture was filtered and filled into air-tight bottles under sterile conditions.

Alternatively, microbiological stabilizers can also be added to the product before filling into bottles.

EXAMPLE 7

After adding 1 m$^3$ of boiling water to 100 kg of purified, dried and ground, leaved alfalfa stalk, the mixture was decocted under slow stirring. After filtration the solution was evaporated to a final volume of 50 liters under reduced pressure and the concentrate obtained was extracted 5 times with 5 liters of n-butanol each. After combining the butanolic extracts were evaporated to dryness. The residue obtained was finely ground, suspended in linseed oil of 30-fold weight (of a pharmacopoeial quality) or in a native oil containing identical oleic acid components or in cod-liver oil or their mixture and then encapsulated in soft gelatine according to the known methods of the pharmaceutical industry.

EXAMPLE 8

A grist prepared from 40 kg of dried alfalfa root and 60 kg of dried alfalfa shoot were heated with 500 liters of water containing 12 g/liter of malic acid in an autoclave at 120° C. for 30 minutes. The extract obtained was separated from the plant residue in a sack centrifuge, concentrated to a dry material content of 14–16% by weight under reduced pressure and finally lyophilized.

The granulate obtained was compressed to tablets or used for preparation of hard-gelatine capsules.

I claim:

1. A process for the preparation of a selective blood-lipid-level-lowering pharmaceutical composition, which comprises extracting the seed, root, stalk or leaves of alfalfa with water or an aqueous solution at a temperature of at least 40° C. and a pH of at most 8, the resulting extract containing at most 1 ppm of canavanin and at most 9 ppm of coumestrol.

2. A process as defined in claim 1, which comprises carrying out the extraction with an aqueous solution at a temperature of 50°-120° C. and a pH of 5.5-6.5.

3. A process as defined in claim 2, which comprises carrying out the extraction with an aqueous solution at a temperature of 60°-70° C. and a pH of 5.8-6.2.

4. A process as defined in claim 1, wherein the aqueous solution comprises hydrochloric, acetic, citric, malic, tartaric, succinic or ascorbic acid.

5. A process as defined in claim 1, wherein the aqueous solution comprises the salt of hydrochloric, acetic, citric, malic, tartaric, succinic, ascorbic or sulfuric acid formed with iron, magnesium, calcium, manganese, selenium, zinc, cobalt or copper ions.

6. A process as defined in claim 1 wherein the aqueous solution comprises the salt of iron, magnesium, calcium, manganese, selenium, zinc, cobalt or copper ion formed with aspartic or glutamic acid.

7. A process as defined in claim 1 wherein the aqueous solution comprises an acidic buffer solution.

8. A process as defined in claim 1 wherein the aqueous solution comprises acetic acid and sodium acetate, potassium dihydrogen phosphate and disodium hydrogen phosphate, disodium hydrogen phosphate and citric acid or sodium acetate as an acidic buffer solution.

9. A process as defined in claim 1, in which the extract is concentrated.

10. A process as defined in claim 9, in which a dried powder or granulate is prepared from the concentrated extract.

11. A selective blood-lipid-level-lowering composition prepared by the process as defined in claim 1.

12. The composition of claim 11, wherein the active ingredients, either alone or together with polysaccharides which are not digestible, or only slightly so, are mixed with pharmaceutically acceptable carriers, wetting agents, sweeteners, aromatizers, buffers or mixtures thereof.

13. An alfalfa extract for selectively lowering the blood-lipid level, containing at most 1 ppm of canavanin and at most 9 ppm of coumestrol.

* * * * *